United States Patent
Jewell et al.

(10) Patent No.: US 10,674,747 B2
(45) Date of Patent: Jun. 9, 2020

(54) ANTI-AGING FOODS FOR COMPANION ANIMALS

(71) Applicant: Hill's Pet Nutrition, Inc., Topeka, KS (US)

(72) Inventors: Dennis Jewell, Lawrence, KS (US); Jeffrey Brockman, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 934 days.

(21) Appl. No.: 14/651,687

(22) PCT Filed: Dec. 14, 2012

(86) PCT No.: PCT/US2012/069609
§ 371 (c)(1),
(2) Date: Jun. 12, 2015

(87) PCT Pub. No.: WO2014/092716
PCT Pub. Date: Jun. 19, 2014

(65) Prior Publication Data
US 2015/0313261 A1 Nov. 5, 2015

(51) Int. Cl.
*A23K 50/40* (2016.01)
*A23K 10/20* (2016.01)
*A23K 10/30* (2016.01)

(52) U.S. Cl.
CPC .............. *A23K 10/20* (2016.05); *A23K 10/30* (2016.05); *A23K 50/40* (2016.05)

(58) Field of Classification Search
CPC ........ A23K 50/40; A23K 50/42; A23K 50/45; A23K 50/48; A23K 10/20; A23K 10/30
See application file for complete search history.

(56) References Cited

U.S. PATENT DOCUMENTS

| | | | |
|---|---|---|---|
| 4,006,266 A * | 2/1977 | Bone | A23K 40/20 426/623 |
| 5,339,771 A | 8/1994 | Axelrod | |
| 5,419,283 A | 5/1995 | Leo | |
| 5,932,258 A * | 8/1999 | Sunvold | A23K 10/30 426/2 |
| 6,177,107 B1 * | 1/2001 | Watson | A23K 20/174 424/643 |
| 6,517,877 B2 | 2/2003 | Gannon | |
| 6,974,841 B1 | 12/2005 | Rapisarda | |
| 7,115,297 B2 | 10/2006 | Stillman | |
| 7,368,481 B1 | 5/2008 | Rapisarda | |
| 7,687,650 B2 | 3/2010 | Ramirez et al. | |
| 7,897,800 B2 | 3/2011 | Ramirez et al. | |
| 7,927,614 B2 | 4/2011 | Faryniarz et al. | |
| 8,142,810 B2 | 3/2012 | Sunvold et al. | |
| 8,148,563 B2 | 4/2012 | Ramirez et al. | |
| 8,273,791 B2 | 9/2012 | Ramirez et al. | |
| 8,952,052 B2 | 2/2015 | Frantz | |
| 2001/0018067 A1 | 8/2001 | Sunvold | |
| 2001/0043983 A1 | 11/2001 | Hamilton | |
| 2003/0064104 A1 | 4/2003 | Stillman | |
| 2003/0179174 A1 | 9/2003 | Matsuda et al. | |
| 2003/0198661 A1 | 10/2003 | Harper et al. | |
| 2004/0001875 A1 | 1/2004 | Sunvold et al. | |
| 2006/0200320 A1 | 9/2006 | Al-Murrani | |
| 2006/0228448 A1 * | 10/2006 | Boileau | A23K 40/20 426/61 |
| 2007/0202073 A1 | 8/2007 | Fenyvesi et al. | |
| 2007/0237880 A1 * | 10/2007 | Coleman | A23L 7/126 426/620 |
| 2008/0317884 A1 * | 12/2008 | Jewell | A61K 31/205 424/736 |
| 2009/0017156 A1 * | 1/2009 | Yu | A23K 10/30 426/2 |
| 2010/0233320 A1 | 9/2010 | Sunvold et al. | |
| 2010/0310750 A1 * | 12/2010 | She | A23K 40/20 426/578 |
| 2010/0330062 A1 | 12/2010 | Koeffler et al. | |
| 2011/0020464 A1 | 1/2011 | Ushijima | |
| 2011/0123669 A1 * | 5/2011 | Yamka | A23K 1/1846 426/2 |
| 2011/0159500 A1 * | 6/2011 | Khoo | C12Q 1/6883 435/6.12 |
| 2011/0318375 A1 | 12/2011 | Melling et al. | |

(Continued)

FOREIGN PATENT DOCUMENTS

| | | |
|---|---|---|
| CN | 101917868 | 12/2010 |
| CN | 102271676 | 12/2011 |

(Continued)

OTHER PUBLICATIONS

Blagosklonny, "Validation of anti-aging drugs by treating age-related diseases," Aging, 2009, 1(3):281-285.
International Search Report and Written Opinion for International Application No. PCT/US2012/069609 dated Jul. 4, 2013.
International Search Report and Written Opinion for International Application No. PCT/US2012/069611 dated Jul. 4, 2013.
Murray et al., "Raw and rendered animal by-products as ingredients in dog diets," J. Anim. Science, 1997, 75(9):2497-2505.
Yamamoto et al., "Regulation of Oxidative Stress by the Anti-aging Hormone Klotho," J. Biol. Chem., 2005, 280(45):38029-38034.

(Continued)

*Primary Examiner* — Walter A Moore

(57) ABSTRACT

The present invention encompasses compositions and methods for the prevention and treatment of age related conditions in animals, particularly in companion animals, in need thereof. The methods for treating or preventing an age-related condition in an animal in need thereof, comprise administering to the animal an effective amount of a composition comprising at least one of a protein source, a carbohydrate source, a vegetable source, a fruit source, or a combination of two or more thereof. In this method, the protein source is selected from the group consisting of chicken, egg protein, corn gluten meal, and combinations thereof; the carbohydrate source is selected from the group consisting of millet, brewers rice, oat groats, and combinations thereof, the vegetable source is selected from the group consisting of carrots, spinach, tomato pomace, and combinations thereof, wherein the fruit source is citrus pulp.

22 Claims, No Drawings

(56) References Cited

U.S. PATENT DOCUMENTS

| | | |
|---|---|---|
| 2012/0040855 A1 | 2/2012 | Pan et al. |
| 2012/0164265 A1 | 6/2012 | Sunvold et al. |
| 2012/0172314 A1 | 7/2012 | Koeffler et al. |

FOREIGN PATENT DOCUMENTS

| | | |
|---|---|---|
| CN | 101198259 | 5/2014 |
| WO | WO 2001/017366 | 3/2001 |
| WO | WO 01/58271 | 8/2001 |
| WO | WO 2007/009111 | 1/2007 |
| WO | WO 2007/070701 | 6/2007 |
| WO | WO 2011/011472 | 1/2011 |
| WO | WO 2012/100991 | 8/2017 |

OTHER PUBLICATIONS

Li et al., eds., 1995, "Relationship of Senescence and Senile Diseases," in Chinese Traditional Treatment of Common Senile Diseases pp. 21-22, 27.

* cited by examiner

ANTI-AGING FOODS FOR COMPANION ANIMALS

BACKGROUND OF THE INVENTION

Aging has been defined as an increase in the probability of death. However, aging, per se, is a natural process, not a medical condition. Although aging is by definition accompanied by an eventual physiological decline, it can be readily observed that the rate of progression and the consequences of this process are not necessarily uniform between animal genera and species, and even between and among individual members of an animal species. The rate of physiological decline and the overall health of an individual aging animal appear to reflect the influence of not only ill-defined genetic determinants but also environmental factors.

Animals may be afflicted with one or more conditions that appear to be age-related and that individually and collectively affect the overall health and longevity of the individual animal as it ages. It has been suggested that animals do not die of "healthy aging" but rather they die from these age-related diseases. Illustrative age-related conditions of canines include, inter alia, deterioration of muscle protein, deterioration of cartilage, accumulation of body fat and/or a decrease in lean body mass, deterioration in kidney health, untoward, inappropriate or excessive inflammatory responses, gastrointestinal health conditions and oxidative damage.

Accordingly, there is a need for compositions and methods for treatment and amelioration of those age-associated conditions that would support "healthy aging," providing the treated animal with a healthier and/or longer life.

BRIEF SUMMARY OF THE INVENTION

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

The present invention encompasses compositions and methods for the prevention and treatment of age-related conditions in animals, particularly in companion animals, in need thereof.

The methods for treating or preventing an age-related condition in an animal in need thereof, comprise administering to the animal an effective amount of a composition comprising at least one of a protein source, a carbohydrate source, a vegetable source, a fruit source, or a combination of two or more thereof. In this method, the protein source is selected from the group consisting of chicken, egg protein, corn gluten meal, and combinations thereof the carbohydrate source is selected from the group consisting of millet, brewers rice, oat groats, and combinations thereof, the vegetable source is selected from the group consisting of carrots, spinach, tomato pomace, and combinations thereof, and wherein the fruit source is a citrus pulp.

In one embodiment of the method, the age-related condition is one of deterioration of muscle protein, deterioration of cartilage, accumulation of body fat and/or a decrease in lean body mass, deterioration in kidney health, untoward, inappropriate or excessive inflammatory responses, gastrointestinal health conditions and oxidative damage. In specific aspects of this embodiment, the age-related condition is one of inappropriate immune response, gastrointestinal disease, excess muscle protein degradation, excess cartilage degradation, oxidative damage, or a combination of two or more thereof.

In another embodiment, the animal is a companion animal. In one aspect of this embodiment, the companion animal is a canine or a feline. In a specific aspect, the animal is a canine.

In other embodiments of the method, the administered composition is a nutritionally complete diet for an adult companion animal. In one aspect of this embodiment, the administered composition is a nutritionally complete diet for an adult canine while, in another, the administered composition is a nutritionally complete diet for an adult feline.

In particular embodiments, practice of the method results in an improvement in at least one of skin condition, coat and/or fur condition (e.g., alopecia), gut health, protein metabolism, cartilage metabolism, immune system function, oxidative defenses, mineral transport, or a combination of two or more thereof, in the treated animal. In specific aspects, the method of prevention or treatment results in at least one of delayed hypersensitivity response, decreased waste production, decreased p-cresol accumulation, decreased 3-methyl histidine accumulation, decreased 4-hydroxyproline accumulation, increased proteasome-1 levels, increased peroxiredoxin-1 levels, increased ceruloplasmin levels, or a combination of two or more thereof, in the treated animal.

The invention also encompasses compositions for treating or preventing an age-related condition in an animal in need thereof, where the composition comprises a protein source, a carbohydrate source, a vegetable source, a fruit source, or a combination of two or more thereof. In this embodiment, the protein source is selected from the group consisting of chicken, egg protein, corn gluten meal, and combinations thereof, the carbohydrate source is selected from the group consisting of millet, brewers rice, oat groats, and combinations thereof, the vegetable source is selected from the group consisting of carrots, spinach, tomato pomace, and combinations thereof, and wherein the fruit source is a citrus pulp.

In certain embodiments, the compositions of the present invention are nutritionally complete diets for an adult companion animal. In, particular aspects of this embodiment, the composition is a nutritionally complete diet for a canine while in another aspect the composition is a nutritionally complete diet for a feline.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

The present invention is directed to compositions and methods for treating or preventing an age-related condition in an animal in need thereof. Compositions of the invention, effective amounts of which are administered in the methods of the invention, include at least one of a protein source, a carbohydrate source, a vegetable source, a fruit source, or a combination of two or more thereof, wherein the protein source is selected from the group consisting of chicken, egg protein, corn gluten meal, and combinations thereof, wherein the carbohydrate source is selected from the group consisting of millet, brewers rice, oat groats, and combinations thereof, wherein the vegetable source is selected from the group consisting of carrots, spinach, tomato pomace, and combinations thereof, and wherein the fruit source is a citrus pulp.

Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication, which might be used in connection with the invention.

As used herein and in the appended claims, the singular forms "a", "an", and "the" include plural reference unless the context clearly dictates otherwise.

As used herein, the term "animal" refers to companion animals. In a specific embodiment, the animal is a domesticated companion animal or "house" pet, such as canine or a feline. In one aspect, the animal is a cat. In another aspect the animal is a dog.

According to the invention, the phrase "animal in need thereof," refers to a companion animal for whom or for which treatment, prevention, or control of an age-related condition is indicated. Such animals include those known to be currently exhibiting the symptoms of or known to be afflicted with an age-related condition, as well as those known to be or expected to be at risk of developing an age-related condition. Animals known to or expected to be at risk of developing an age-related condition include, for example, members of species or subgroups thereof, that are known or inferred to carry one or more genetic determinants associated with the very occurrence or that earlier onset or rate of development of one or more age-related conditions, as compared to members of closely-related genera, species and/or subgroups thereof.

The term "preventing," as used herein, means e.g., to completely or almost completely stop, as well as to substantially reduce development or progression of an age-related condition by the animal in need thereof.

The term "treating," as used herein, means to cure, inhibit, arrest the development, relieve the symptoms or effects of, or to ameliorate, or cause the reduction in the symptoms or effects of an age-related condition in an animal in need of methods disclosed herein. Accordingly, it should be recognized that the terms "preventing," treating," and "controlling," are not intended to limit the scope of the invention and that, although distinguishable from one another, there can be overlap amongst these terms.

The term "companion animal" used in the present invention includes any non-human animal suitable for being kept as a pet by humans including without limitation, a dog, a cat, rabbit and a rodent. Specific embodiments of the present invention are formulations and methods of treatment for dogs and/or cats. In one specific aspect, the present invention is directed to formulations and methods of treatment for dogs.

The term "dog" includes those dogs which are companion animals such as *Canis familiaris*, working dogs and the like. The term dog is synonymous with the term canine.

The term "cat" includes those cats which are companion animals known as domestic cats or house cats, or *Felis domesticus*. The term cat is synonymous with the term feline.

As used herein, "an amount effective," "an effective amount," and like terms refer to that amount of a material or composition as described herein that may be effective to achieve a particular biological result, i.e., prevention, treatment, or amelioration of an age-related condition. In specific embodiments, administration of an effective amount of a composition of the invention will be for a time sufficient to prevent, treat, or ameliorate an age-related condition or one or more effects or manifestations thereof in the animal treated. In a particular embodiment, the method comprises administration and consumption of a composition of the invention for a period of time sufficient to result in prevention, treatment, or amelioration of an age-related condition or one or more effects thereof in the animal treated to a level acceptable to the owner of a non-human animal in need of the methods of prevention and treatment disclosed herein. An effective amount may be based on several factors, including an animal's ideal weight, the age, gender, and activity of the animal, the metabolizable energy of the composition, and the frequency of feeding the compositions of the present invention, e.g., once, twice, or three times daily, and other compositions fed to the animal.

A "food," "food composition," or "pet food composition" can, in some embodiments of the invention, be a nutritionally complete diet for the intended recipient companion animal, e.g., a domestic cat or domestic dog.

As used herein, an "ingredient" refers to any component of a composition.

The term "nutrient" refers to a substance that provides nourishment. In some cases an ingredient may comprise more than one "nutrient," for example, a composition may comprise corn comprising important nutrients including both protein and carbohydrate.

As contemplated herein, the compositions of the present invention are meant to encompass, but not be limited to, nutritionally-complete and balanced animal food compositions. A "nutritionally complete diet" is a diet that includes sufficient nutrients for maintenance of normal health of a healthy animal on the diet. Nutritionally complete and balanced pet food compositions, e.g., for companion felines and canines, are familiar to one of skill in the art. For example substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga. (2012).

As used herein, the term "supplement(s)" include, but are not limited to, a feed used with another feed to improve nutritive balance or performance of the total diet for an animal. Supplements include, but are not limited to, compositions that are fed undiluted as a supplement to other feeds, offered free choice with other parts of an animal's ration that are separately available, or diluted and mixed with an animal's regular feed to produce a complete feed. The AAFCO guidelines, for example, contain a discussion relating to supplements in the Official Publication of the Association of American Feed Control Officials, Inc. (AAFCO), Atlanta, Ga. (2012). Supplements may be in various forms including, for example, powders, liquids, syrups, pills, encapsulated compositions and the like.

"Bioactive dietary components" (BDCs) may include amino acids, simple and complex sugars, vitamins, cofactors, antioxidants, omega-3 fatty acids, various botanical preparations, etc. Certain materials can be considered BDCs that may contain one or more bioactive components that, whether known or unknown, may additively or synergistically contribute to the bioactive effect of the material.

Aging is the natural process in animals that is characterized by progressive degenerative changes in tissue organization and function that increase the probability of mortality. Associated with the natural aging process are age-related condition, the age of onset, development, and rate of progression of which have both genetic and environmental components. Accordingly, age-related conditions include those conditions that observed in and associated with older, aging animals, at least as compared to younger animals of the same genus and species. Illustrative, non-limiting examples of age-related conditions include deterioration of muscle protein, deterioration of cartilage, accumulation of body fat and/or a decrease in lean body mass, deterioration in kidney health, untoward, inappropriate or excessive inflammatory responses, gastrointestinal health conditions, oxidative damage, deterioration in the condition of the skin and/or coat condition (e.g., alopecia), or a combination of two or more thereof. The age of onset, development, and rate of progression of such age-related conditions, may vary substantially between and among members of the same species.

Compositions and Formulations

Application of the methodology outlined above has identified bioactive dietary components that have been combined to provide compositions, foods, and diets that provide significant anti-aging benefits to animals, e.g., to companion animals such as canines and felines, and, in a particular embodiment, to domesticated dogs. When administered to animals in need thereof, these compositions, foods, and diets are observed to reduce inappropriate skin response to the animal's environment, to provide improvements in gastrointestinal health, protein degradation, cartilage degradation and/or oxidative damage to the treated animals. These studies identified three protein sources (chicken, egg protein, and corn gluten meal) as useful in compositions administered in the presently-described methods for the prevention and/or treatment of age-related conditions in animals, e.g., canines and felines, and in particular, in companion canines. These studies also identified three carbohydrate sources (millet, brewers rice, and oat groats) as well as specific vegetables (carrots, spinach, and tomato pomace) and specific fruit ingredients (citrus pulp) useful in the compositions administered in the presently disclosed methods, Accordingly, compositions of the invention, which are administered in the methods described herein for prevention and/or treatment of an age-related condition in an animal in need thereof, comprise a protein source, a carbohydrate source, a vegetable source, a fruit source, or a combination of two or more thereof. The protein source is selected from the group consisting of chicken, egg protein, corn gluten meal, and combinations thereof, while the carbohydrate source is selected from the group consisting of millet, brewers rice, oat groats, and combinations thereof. The vegetable source is selected from the group consisting of carrots, spinach, tomato pomace, and combinations thereof, and the fruit source is citrus pulp.

Particular embodiments of the present invention are directed to mixtures of these bioactive dietary components as ingredients to provide compositions and formulations that, when administered to an animal in need thereof, impart specific anti-aging effects.

In one aspect of these embodiments, the compositions comprise chicken in an amount from 5% to 25% based on the total weight of the composition on a dry matter basis.

In one aspect of these embodiments, the compositions comprise egg protein in an amount from 4% to 15% based on the total weight of the composition on a dry matter basis.

In another aspect, the compositions comprise corn gluten meal in an amount from 6% to 20% based on the total weight of the composition on a dry matter basis.

In still another aspect of these embodiments, the compositions comprise carrots, spinach, tomato pomace, and combinations thereof, in an amount from 0.5% to 2% based on the total weight of the composition on a dry matter basis.

In a further aspect of these embodiments, the compositions comprise citrus pulp in an amount from 0.5% to 2% based on the total weight of the composition on a dry matter basis.

In another embodiment, compositions of the invention comprise a carbohydrate selected from millet, brewers rice, oat groats, and combinations thereof in an amount of 5% to 50% based on the total weight of the composition on a dry matter basis.

In certain embodiments, compositions of the invention comprise chicken in an amount of 5%, 7.5%, 10%, 12.5%, 15%, 17.5%, 20%, 22.5% or 25% based on the total weight of the composition on a dry matter basis. In particular aspects of these embodiments, compositions of the invention may comprise a dry weight of chicken within a range defined by any two of these values as endpoints.

In certain embodiments, compositions of the invention comprise egg protein in an amount of 4%, 5%, 6%, 7%, 8%, 9%, 10%, 11%, 12%, 13%, 14% or 15% based on the total weight of the composition on a dry matter basis. In particular aspects of these embodiments, composition of the invention may comprise a dry weight of egg protein within a range defined by any two of these values as endpoints.

In certain embodiments, compositions of the invention comprise corn gluten meal in an amount of 6%, 7%, 8%, 9%, 10%, 11%, 12%, 13%, 14%, 15%, 16%, 17%, 18%, 19%, or 20% based on the total weight of the composition on a dry matter basis. In particular aspects of these embodiments, composition of the invention may comprise a dry weight of corn gluten meal within a range defined by any two of these values as endpoints In certain embodiments, compositions of the invention comprise a vegetable source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In particular aspects of these embodiments, composition of the invention may comprise a dry weight of a vegetable source within a range defined by any two of these values as endpoints.

In certain embodiments, compositions of the invention comprise a fruit source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In particular aspects of these embodiments, composition of the invention may comprise a dry weight of a citrus pulp within a range defined by any two of these values as endpoints.

In certain embodiments, compositions of the invention comprise a carbohydrate selected from millet, brewers rice, oat groats, and combinations thereof in an amount of 5%, 10%, 15%, 20%, 25%, 30%, 35%, 40%, 45%, or 50% based on the total weight of the composition on a dry matter basis. In particular aspects of these embodiments, composition of the invention may comprise a dry weight of a carbohydrate source within a range defined by any two of these values as endpoints.

In other aspects of this embodiment, the food product is a nutritionally complete diet for an adult companion animal, e.g., an adult canine or an adult feline companion animal. In a specific aspect, the food product is a nutritionally complete diet formulated for an adult companion canine.

In other aspects of this embodiment, the food product is a nutritionally complete diet for an aged companion animal, e.g., an aged canine or an adult feline companion animal. In a specific aspect, the food product is a nutritionally complete diet formulated for an aged companion canine.

In another aspect of this embodiment, the food comprises from 5% to 50% carbohydrate, by dry weight of the composition, selected from millet, brewers rice, oat groats, and combinations thereof.

Compositions of the present invention include food compositions that may comprise protein in an amount from 4% to 75% based on the total weight of the composition on a dry matter basis, fat in an amount from 5% to 50% based on the total weight of the composition on a dry matter basis, and carbohydrate from 5% to 75% based on the total weight of the composition on a dry matter basis, wherein the food composition is suitable for consumption by an animal, and wherein the composition is effective for prevention and/or treatment of an age-related condition in an animal in need thereof.

The compositions of the invention, which are administered in the methods of the invention, may be formulated as an animal food composition that, in certain embodiments, is a nutritionally-balanced and/or nutritionally-complete animal food product or diet. In other embodiments, the composition is formulated and prepared as a nutritional supplement, a treat, or a toy.

For example, a nutritionally complete and balanced cat food composition of the present invention may comprise: from 4% to 90%, from 5% to 75%, from 10% to 60% protein, and from 15% to 50% by weight of protein; from 0% to 75%, from 2% to 60%, and from 5% to 50% by weight of carbohydrate; from 2% to 60%, from 5% to 50%, and from 10% to 35% by weight of fat. The compositions may further contain from 0 to 15%, or from 2% to 8%, by weight of vitamins (e.g., vitamin E) and minerals, antioxidants, and other nutrients, e.g. amino acids (e.g., methionine, DL-methionine, and L-methionine), which support the nutritional needs of the animal.

For example, a nutritionally complete and balanced dog food composition of the present invention may comprise: from 4% to 90%, from 5% to 75%, from 10% to 60% protein, and from 15% to 50% by weight of protein; from 0% to 90%, from 2% to 80%, from 5% to 75%, and from 10% to 50% by weight of carbohydrate; from 2% to 60%, from 5% to 50%, and from 10% to 35% by weight of fat. The compositions may further contain from 0 to 15% or from 2% to 8%, by weight of vitamins and minerals, antioxidants, and other nutrients which support the nutritional needs of the animal.

Sources of proteins, carbohydrates, fats, vitamins, minerals, balancing agents, and the like, suitable for inclusion in the compositions of the invention, and particularly in the food products of the invention to be administered in the claimed methods, may be selected from among those conventional materials known to those of ordinary skill in the art.

Proteins useful as ingredients of the food compositions of the present invention may, in addition to one or more of chicken, e protein, and corn gluten meal, be from any source, including, for example, proteins from animal sources, such as meat protein isolate, whey protein isolate, mixtures thereof and the like, as well as vegetable sources, such as soy protein isolate, corn, wheat gluten, mixtures thereof, and the like. Additional sources of protein may include one or more of the following: animal proteins, including mammalian, avian protein, reptilian, amphibian, fish, invertebrate proteins and combinations thereof; e.g., from any of cattle, sheep, pig, goat, deer, rabbit, horse, kangaroo, their milk, curds, whey or blood, and internal tissues and organs such as smooth muscle, striate muscle, liver, kidney, intestine or heart; additional avian protein sources encompass turkey, goose, duck, ostrich, quail, pigeon, their eggs and internal tissues and organs such as smooth muscle, striate muscle, liver, kidney, intestine or heart; amphibian sources include frog or salamander, reptilian protein sources include alligator, lizard, turtle and snake; fish protein sources include catfish, herring, salmon, tuna, bluefish, cod, halibut, trout, swordfish and their eggs; and invertebrate protein sources include lobster, crab, clams, mussels or oysters, and combinations thereof.

Carbohydrate components of compositions of the present invention may, in addition to one or more of millet, brewers rice, and oat groats, be from any source, and may enter the food composition as part of another ingredient, such as the protein source. In certain embodiments, carbohydrates useful as ingredients of the food compositions of the present invention include polysaccharides (e.g., starches and dextrins) and sugars (e.g., sucrose, lactose, maltose, glucose, and fructose) that are metabolized for energy when hydrolyzed. Examples of additional carbohydrate sources suitable for inclusion in the compositions disclosed herein include, but are not limited to, corn, whole yellow corn, grain sorghum, wheat, barley, and rice.

Fats useful as ingredients of the food compositions of the present invention may be from any source, such as but not limited to poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods.

In one embodiment, the composition to be administered in the claimed methods is formulated and prepared as a supplement. Supplements include, for example, a food product, feed, or pet food that can be used with another food product feed, or pet food composition to improve the nutritive balance or performance of the total. Contemplated supplements include compositions that are fed undiluted as a supplement to other feeds or pet foods, offered free choice with other parts of an animal's ration that are separately available, or diluted and mixed with an animal's regular feed or pet food to produce a complete feed or pet food. The AAFCO, for example, has provided a discussion relating to supplements in the Official Publication of the Association of American Feed Control Officials, Inc. (2012 Atlanta, Ga.). Supplements may be in various forms including, for example, powders, liquids, syrups, pills, encapsulated compositions, etc.

In another embodiment, treats of the present invention can be prepared by, for example, an extrusion or baking process similar to those described below for dry food to provide an edible product. Treats include, for example, compositions that are given to an animal to entice the animal to eat during a non-meal time. Treats may be nutritional, wherein the composition comprises one or more nutrients, and may, for example, have a composition as described above for food. Non-nutritional treats encompass any other treats that are non-toxic. Compositions of the invention can be coated onto the treat, incorporated into the treat, or both.

In another embodiment, the animal toy is a chewable or consumable toy that is typically prepared by coating any existing toy with a formulation of the invention. Toys therefore include, for example, chewable toys. Contemplated toys for dogs include, for example, artificial bones. In certain embodiments, the composition of the invention can form a coating on the surface of the toy or on the surface of a component of the toy, or it can be incorporated partially or fully throughout the toy, or both. A wide range of suitable toys are currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). It should be recognized that this invention contemplates both partially consumable toys (e.g., toys comprising plastic components) and fully consumable toys (e.g., rawhides and various artificial bones). It should be further recognized that this invention contemplates toys for companion animals and particularly for use by a cat or a dog.

Preparation of the Compositions of the Invention

The compositions of the invention, which are to be administered to animals in need of the methods disclosed herein, may be prepared as food products suitable for consumption by the animals. These food products may be of any consistency or moisture content; i.e., the compositions of the present invention may be moist, semi-moist, or dry food products. "Moist" food products are generally those with a moisture content of from 60% to 90% or greater. "Dry" food products are generally those with a moisture content of from 3% to 11%, and are often manufactured in the form of small pieces or kibbles, "Semi-moist" food products generally have a moisture content of from 25% to 35%. The food products of the present invention may also include components of more than one consistency, for example, soft, chewy meat-like particles or pieces as well as kibble having an outer cereal component or coating and an inner "cream" component, e.g., as described in U.S. Pat. No. 6,517,877.

In certain embodiments, the food products may be prepared in a canned or wet form using conventional food preparation processes known to those of ordinary skill in the art. Typically, ground animal proteinaceous tissues are mixed with the other ingredients, such as cereal grains, suitable carbohydrate sources, fats, oils, and balancing ingredients, including special purpose additives such as vitamin and mineral mixtures, inorganic salts, cellulose, beet pulp and the like, and water in an amount sufficient for processing. The ingredients are mixed in a vessel suitable for heating while blending the components. Heating the mixture is carried out using any suitable manner, for example, direct steam injection or using a vessel fitted with a heat exchanger. Following addition of all of the ingredients of the formulation, the mixture is heated to a temperature of from 10° C. to 100° C. (50° F. to 212° F.). Although temperatures outside this range can be used, they may be commercially-impractical without the use of other processing aids. When heated to the appropriate temperature, the material will typically be in the form of thick liquid, which is dispensed into cans. A lid is applied and the container is hermetically sealed. The sealed can is then placed in convention equipment designed for sterilization of the contents. Sterilization is usually accomplished by heating to temperatures of greater than 230° C. for an appropriate time depending on the temperature used, the nature of the composition, and related factors. The compositions and food products of the present invention can also be added to or combined with food compositions before, during, or after their preparation.

In other embodiments, the food products may be prepared in a dry form using convention processes known to those of ordinary skill in the art. Typically, dry ingredients, including dried animal protein, plant protein, grains and the like are ground and mixed together. Liquid or moist ingredients, including fats, oils, animal protein, water, and the like are added combined with the dry materials. The specific formulation, order of addition, combination, and methods and equipment used to combine the various ingredients can be selected from those known in the art. For example, in certain embodiments, the resulting mixture is process into kibbles or similar dry pieces, which are formed using an extrusion process in which the mixture of dry and wet ingredients is subjected to mechanical work at high pressure and temperature, forced through small openings or apertures, and cut off into the kibbles, e.g., with a rotating knife. The resulting kibble can be dried and optionally coated with one or more topical coatings comprising, e.g., flavors, fats, oils, powdered ingredients, and the like. Kibbles may also be prepared from dough by baking, rather than extrusion, in which the dough is placed into a mold before dry-heat processing.

In preparing a composition for use with the methods of the present invention, any ingredient generally may be incorporated into the composition during the processing of the formulation, e.g., during and/or after mixing of the other components of the composition. Distribution of these components into the composition can be accomplished by conventional means. In certain embodiments, ground animal and/or poultry proteinaceous tissues are mixed with other ingredients, including nutritional balancing agents, inorganic salts, and may further include cellulose, beet pulp, bulking agents and the like, along with sufficient water for processing.

In particular embodiments, the compositions are formulated so as to be easier to chew. In specific embodiments, the compositions and food products are formulated to address specific nutritional differences between species and breeds of animals, as well as one of more of the attributes of the animal. For example, canine and feline foods, for example, are typically formulated based upon the life stage, age, size, weight, body composition, and breed.

Accordingly, in one specific embodiment, the present invention is directed to a method for preparing a food product, the method comprising, admixing suitable sources of protein, fat, carbohydrate, minerals, and vitamins, and processing the mixture to provide the food product, to provide a food product suitable for consumption by an animal, e.g., a companion animal such a feline or canine companion animal, in which the food product comprises a protein source, a carbohydrate source, a vegetable source, a fruit source, or a combination of two or more thereof, in which at least one of (1) the protein source is selected from the group consisting of chicken, egg protein, corn gluten meal, and combinations thereof, (2) the carbohydrate source is selected from the group consisting of millet, brewers rice, oat groats, and combinations thereof, (3) the vegetable source is selected from the group consisting of carrots, spinach, tomato pomace, and combinations thereof, and (4) the fruit source is citrus pulp.

In one particular aspect of this embodiment, the food product comprises chicken in an amount from 5% to 25% based on the total weight of the composition on a dry matter basis.

In one particular aspect of this embodiment, the food product comprises egg protein in an amount from 4% to 15% based on the total weight of the composition on a dry matter basis.

In another aspect of this embodiment, the food product comprises corn gluten meal in an amount from 6% to 20% based on the total weight of the composition on a dry matter basis.

In still another aspect of this embodiment, the food product comprises a vegetable source from 0.5% to 2% based on the total weight of the composition on a dry matter basis.

In another aspect of this embodiment, the food product comprises a fruit source in an amount from 0.5% to 2% based on the total weight of the composition on a dry matter basis.

In another aspect of this embodiment, the food comprises a carbohydrate selected from millet, brewers rice, oat groats, and combinations thereof in an amount from 5% to 50% based on the total weight of the composition on a dry matter basis In other aspects of this embodiment, the food product is a nutritionally complete diet for an adult companion animal, e.g., an adult canine or an adult feline companion animal. In a specific aspect, the food product is a nutritionally complete diet formulated for an adult companion canine.

In other aspects of this embodiment, the food product is a nutritionally complete diet for an aged companion animal, e.g., an aged canine or an adult feline companion animal. In a specific aspect, the food product is a nutritionally complete diet formulated for an aged companion canine.

The compositions of the present invention that are formulated as a nutritionally complete diet meet the needs of a mature adult or an aged animal, such as a companion canine or feline. These nutritionally complete diets that include sufficient nutrients for maintenance of normal health of a healthy animal on the diet. Nutritionally complete and balanced pet food compositions, e.g. for companion canines and felines, are familiar to one of skill in the art. For example substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga. (2012).

Compositions of the present invention include those that, when administered to an animal in need thereof, result in biological effects that offset one or more degradative effects of aging, providing, e.g., improved skin and coat, improved gut health, reduction of excessive degradation of muscle protein, reduction of excessive degradation of cartilage, and specific improvement in the levels of proteins associated with oxidation (peroxiredoxins), mineral transport (ceruloplasmin) and the immune system (proteasome).

Methods of the Invention

The present invention is further directed to methods for treating or preventing an age-related condition in an animal in need thereof. These methods comprise administering to the animal an effective amount of a composition of the present invention that comprises at least one of a protein source, a carbohydrate source, a vegetable source, a fruit source, or a combination of two or more thereof. A protein source to be formulated in a composition administered in these methods can be selected from the group consisting of chicken, egg protein, corn gluten meal, and combinations thereof. A carbohydrate source to be formulated in a composition administered in these methods can be selected from the group consisting of millet, brewers rice, oat groats, and combinations thereof. A vegetable source to be formulated in a composition administered in these methods can be selected from the group consisting of carrots, spinach, tomato pomace, and combinations thereof. A fruit source formulated in a composition administered in these methods can be a citrus pulp.

Age-related conditions prevented and/or treated according to method of the present invention include, without limitation, inappropriate immune response, gastrointestinal disease, excess muscle protein degradation, excess cartilage degradation, oxidative damage, or a combination of two or more thereof.

In certain embodiments, practice of the methods of prevention and/or treatment described herein result in an improvement in at least one of skin condition, coat and/or fur condition, gut health, protein metabolism, cartilage metabolism, immune system function, oxidative defenses, mineral transport, or a combination of two or more thereof, in the treated animal In certain embodiments, practice of the methods of prevention and/or treatment described herein result in delayed hypersensitivity response, decreased waste production, decreased p-cresol accumulation, decreased 3-methyl histidine accumulation, decreased 4-hydroxyproline accumulation, increased proteasome-1 levels, increased peroxiredoxin-1 levels, increased ceruloplasmin levels, or a combination of two or more thereof, in the treated animal.

The animal treated according to the methods described herein is an animal in need of such treatment. In certain embodiments, that animal is a companion animal or a house pet such as canine or a feline. In one aspect, the animal is a cat. In another aspect the animal is a dog.

EXAMPLES

Example 1: Formulation of Anti-Aging Foods

In an initial experiment, three compositions were formulated as canine food compositions having the ingredients provided in Table 1, below.

TABLE 1

| Ingredient | Control | Food A | Food B |
| --- | --- | --- | --- |
| Corn | 66% | 64% | 62% |
| Dried egg product | 0% | 2% | 4% |

All three diets (Control food, Food A, and Food B) contained the same amounts of chicken meal, animal fat, soybean mill run, flax seed, corn gluten meal, palatability enhancer, vitamin E oil, choline chloride, salts, amino acids, vitamins, minerals, and additives.

The Control food did not include egg powder, while Foods A and B contained, respectively 2% and 4% egg powder by dry weight of the composition. Administration of the dried egg powder containing compositions of Table 1

(Foods A and B), inhibited the delayed-type hypersensitivity response in dogs, as compared to Control, as demonstrated in Example 2.

The studies described herein were carried out with a Control group of dogs and a Test group of dogs. The animals of both groups were normal and healthy. The Control group included 27 dogs (14 male and 13 female) having an average age of 10.15 years, with an age range of from 8 to 14 years of age. The Test group also included 27 dogs (16 male and 11 female) having an average age of 10.04 years, with an age range of from 8 to 13 years of age.

Example 2: Delayed Type Hypersensitivity Response

During development of the compositions and methods of the present invention, it was discovered that egg product was a protein source which was specifically beneficial for prevention and/or treatment of age-related conditions. In this Example, delayed type hypersensitivity was investigated by evaluating the hypersensitivity of the older dog, fed either the Control food, Food A, or Food B of Table 1. The hypersensitivity response is gauged after intradermal injection of an aliquot keyhole limpet hemocyanin. In this assay a larger wheal diameter is indicative of a more aggressive response that is deemed to reflect hypersensitivity. In older dogs this can result in diminished skin and coat and/or fur appearance, because this hyper response degrades the overall skin and coat health. The data of Table 2 demonstrate that egg alone can modify the hypersensitivity response, causing a reduction in the severity of the response, in a manner analogous to the response observed when dogs were dosed with prednisone (2.2 mg/kg of prednisone, administered orally every other day) in this assay.

TABLE 2

Wheal Diameter (mm) Observer after Antigen Injection

| Treatment | 0.5 hr. | 24 hr. | 48 hr. | 72 hr. | 96 hr. | 120 hr. |
|---|---|---|---|---|---|---|
| Control | 15.3 $^a$ | 20.3 | 16.4 | 14.8 | 14.9 $^a$ | 15.9 $^a$ |
| Food A | 12.2 $^b$ | 20.4 | 15.8 | 15.0 | 13.4 $^{a,b}$ | 14.0 $^{a,b}$ |
| Food B | 10.4 $^c$ | 17.8 | 14.1 | 15.0 | 12.6 $^b$ | 12.1 $^b$ |
| Prednisone | 10.3 | 15.4 | 12.7 | 14.9 | 12.2 | 12.6 |
| Std. Dev. | 2.0 | 3.6 | 2.6 | 2.5 | 1.7 | 2.0 | a,b,c Means within a column that do not share a common superscript are significantly different. Prednisone was administered to a group which resulted in a decrease in the delayed type hypersensitivity response.

The data of Table 2 established that feeding the canines a diet formulated with dried egg product reduced the delayed type hypersensitivity response.

This benefit was also illustrated by the observed improvement in the overall skin and coat quality of the treated animals fed a composition of the invention in a 180 day feeding study. These improved ratings of overall skin and coat were noted after feeding a food of the invention that contained a sufficient amount of egg for reduction of the delayed type hypersensitivity response. More specifically, after 180 days of feeding the test animals a food composition of the invention comprising 7% egg, the treated canines displayed an improvement in skin and coat evaluations. The data obtained are presented in Table 3, below, where a smaller number is indicative of an improvement in the skin and/or coat of the treated dogs.

TABLE 3

Skin and Coat Measurements

|  | Day 0 | Day 45 | Day 90 | Day 180 |
|---|---|---|---|---|
| Mean Score | 2.33 | 2.08 | 1.96 | 2.08 |
| Standard Error | 0.07 | 0.07 | 0.07 | 0.07 |

The data of Table 3 demonstrate that, after 180 days of feeding the test animals a food composition of the invention comprising 7% egg, the treated canines displayed improved skin and coat improvement of 0.25 points (Std. Error 0.10) on a five-point scale in which a one point movement was a subjective change from good to excellent.

Accordingly, administration of a composition of the invention is useful as a method for prevention and/or treatment of age-related conditions involving inappropriate immune response, and/or deterioration in the skin, coat, and/or fur condition, of an animal in need thereof.

Example 3: Pre-Feed, Control, and Anti-Aging Food Compositions

The foods administered to the canines in the Examples below include a Pre-feed composition provided to the animals before initiation of the studies, as well as a Control Food and an illustrative Anti-Aging Food of the invention administered in the studies. The levels of moisture, ash, protein, crude fat, fiber, and total fatty acids in these foods are provided in Table 4, below.

TABLE 4

| Ingredient | Pre-Feed | Control Food | Anti-Aging Food |
|---|---|---|---|
| Moisture | 9.3% | 8.0% | 7.1% |
| Ash | 4.6% | 4.8% | 4.2% |
| Crude Fat | 8.9% | 15.3% | 14.0% |
| Crude Fiber | 1.5% | 3.6% | 1.0% |
| Crude Protein | 20.1% | 19.3% | 18.0% |
| Total Fatty Acids | 7.5% | 14.1% | 12.0% |
| Carbohydrate* | 55.6% | 49.1% | 55.7% |

*Carbohydrate (Nitrogen-free extract) ≡ 100% − (% Protein + % Fat % Ash + % Fiber + % Moisture)

The Anti-Aging Food was formulated with protein sources that included chicken, egg protein, and corn gluten meal, carbohydrate sources including millet, brewers rice, and oat groats, and vegetable sources including carrots, spinach, and tomato pomace, as well as citrus pulp. Although similar in overall composition, the Control Food did not include the combination of chicken, egg protein, corn gluten meal, millet, brewers rice, oat groats, carrots, spinach, tomato pomace, and citrus pulp, much less each within the concentrations described herein. That is, although the Control and Anti-Aging Foods are both formulated to meet the nutritional requirements of the canines to be fed those compositions, the sources of ingredients used to formulate those diets differ from one another.

Example 4: Improved Gastrointestinal Health

This Example demonstrates that feeding canines the Anti-Aging Food of Table 4 resulted in a reduction of fecal waste produced by the treated animals as well as an improvement in the level of a biological marker of gastrointestinal health (p-cresol), as compared to the results observed with control animals provided with the Control Food. The data generated in this Example are set forth in Table 5, below.

TABLE 5

Waste Reduction

|  | 0-45 Days | 45-90 Days | 90-180 Days | Total Intake (kilograms) | Daily Aver. (grams) | Fecal dry wt. as % food intake |
|---|---|---|---|---|---|---|
| Animals Fed The Control Food | | | | | | |
| Average Total Food Intake | 256 | 247 | 253 | 45.4 | 252 | |
| Average Food Intake (dry weight) | 234.5 | 226.3 | 231.7 | — | 231 | |
| Average Waste (dry weight) | 40.6 | 39.1 | 43.8 | — | 40.0 | 17.3% |
| Animals Fed The Anti-Aging Food | | | | | | |
| Average Total Food Intake | 235 | 236 | 263 | 44.9 | 249 | |
| Average Food Intake (dry weight) | 217.8 | 218.8 | 243.8 | — | 231.1 | |
| Average Waste (dry weight) | 26.6 | 26.7 | 32.1 | — | 28.2 | 12.2% |

With respect to reduction in generation of waste reduction (measured as dry matter), the data of Table 5 demonstrate that animals fed the Control Food generated approximately 40 g/day waste (dry weight) per day as compared to the 28 g/day generated by animals fed the Anti-Aging Food of Table 4, which represents a 30% improvement.

With respect to the improvement in the level of a marker associated with gastrointestinal health, it was observed that blood levels of a toxic microbial product (p-cresol) were lower in animals provided canines the Anti-Aging Food of Table 4 than were observed in control animals provided with the Control Food.

Metabolite levels were determined by a commercial laboratory (Metabolon, Inc., Durham, N.C.). Serum samples were solvent-extracted and analyzed by mass spectroscopy and either gas chromatography (hydrophobic molecules), or liquid chromatography (hydrophilic molecules). Data for the metabolites of interest were normalized by calculating the median values for each run-day block ("block normalization"), to minimize any potential inter-day drift in instrument gain, without interfering with intra-day sample variability. These data are provided in Table 6 below.

TABLE 6

Relative Blood Levels of p-Cresol Sulfate

| Treatment Group | Day 0 | Day 45 | Day 90 |
|---|---|---|---|
| Control Food | 1 | 0.94 | 0.85 |
| Anti-Aging Food | 1 | 0.62 | 0.72 |

The data of Table 6 demonstrate that both groups of dogs experienced a significant decline in this toxic compound (p-cresol sulfate). The ratios in Table 5 were calculated by dividing the amount of p-cresol sulfate observed on the treatment day by the amount at day zero. Administration of the Anti-Aging Food, however, resulted in a greater decline in this toxic substance at both time points, as compared to the Control Food.

Accordingly, administration of an Anti-Aging Food of the invention is useful as a method for prevention and/or treatment of age related conditions involving deterioration in gut health in a companion animal in need thereof.

Example 5: Improvement in Resistance to Oxidative Stress

It has also been observed that feeding animals a composition of the invention results in improved levels of three specific proteins, peroxiredoxin-1, ceruloplasmin, and proteasome-1, each of which is associated with amelioration of oxidative stress in aging dogs. Determination of the levels of each was carried out using standard laboratory reagents, assays, and protocols.

For example, there is a 3.11-fold decrease in peroxiredoxin-1 levels in older dogs as compared to levels of that protein in young adult dogs. This age-related change was completely offset by feeding an Anti-Aging Food of Table 4, which resulted in a 3.92-fold increase in peroxiredoxin-1 levels after 180 days, as compared to the levels observed in animals fed the Control Food. The data obtained demonstrate the almost four-fold increase in peroxiredoxin-1 levels in the dogs fed Anti-Aging Food as compared to the Control Food.

With respect to mineral transport, it was observed that there was a 1.73-fold decrease in the levels of Ceruloplasmin (a copper transport protein) in aging dogs as compared to young dogs. The data obtained demonstrate that dogs fed the Anti-Aging Food of Table 4 exhibited a 2.15-fold increase in ceruloplasmin levels after 180 days.

The reduction in immune competence of the older dog was shown by the reduction in Proteasome-1 which was also offset by 180 days of feeding the Anti-Aging Food (a 1.4 fold decline in aging dogs (vs. young dogs), as compared to an observed 1.39 increase after feeding the dogs the Anti-Aging Food of Table 4).

All three of these proteins had lesser changes when fed the Control Food for 180 days.

The data of Table 7, below, present the fold-difference in ceruloplasmin, peroxiredoxins-1, and proteasome levels observed in aged dogs as compared to the levels observed in adult dogs.

TABLE 7

Effect of Aging on Ceruloplasmin, Peroxiredoxins-1, and Proteasome Levels

|  | Ceruloplasmin | Peroxiredoxins-1 | Proteasome |
|---|---|---|---|
| Fold Difference (Old vs. Young) | −1.73 | −3.11 | −1.40 |
| P-value | 0.001 | 0.000 | 0.017 |

As demonstrated by the data obtained, the levels of each of ceruloplasmin, peroxiredoxins-1, and proteasome are depressed in the aging animal. These effects of feeding the aging canines the Anti-Aging Food of Table 4 on ceruloplasmin, peroxiredoxins-1, and proteasome levels are presented in Table 8 below.

TABLE 8

Effect of Anti-Aging Food on Ceruloplasmin, Peroxiredoxins-1, and Proteasome Levels

| | Ceruloplasmin | | Peroxiredoxins-1 | | Proteasome | |
|---|---|---|---|---|---|---|
| | Day 90 | Day 180 | Day 90 | Day 180 | Day 90 | Day 180 |
| Animals Fed The Control Food | | | | | | |
| Fold | 1.16 | 1.48 | −1.34 | 1.50 | 1.22 | 1 |
| P-Value | 0.625 | 0.230 | 0.713 | 0.269 | 0.388 | 0.745 |
| Animals Fed The Anti-Aging Food of Table 4 | | | | | | |
| Fold | 1.20 | 2.15 | 2.39 | 3.92 | 1.17 | 1.39 |
| P-Value | 0.391 | 0.028 | 0.049 | 0.027 | 0.229 | 0.029 |

As noted above, the levels of each of ceruloplasmin, peroxiredoxins-1, and proteasome are depressed in the aging animal. However, as demonstrated by the data of Table 8, feeding dogs the Anti-Aging Food of Table 4 resulted in the reversal of this trend, with the levels of each of ceruloplasmin, peroxiredoxins-1, and proteasome rising markedly as compared to base-line data as well as the data obtained with dogs provided the Control Food. Since each of these enzymes is involved in the body's defenses to oxidative stress, administration of a composition of the invention is useful as a method for prevention and/or treatment of age-related conditions involving oxidative stress in a companion animal in need thereof.

Example 6: Improvement in Muscle and Cartilage Metabolism

This Example demonstrates that feeding canines a composition of the invention results in a reduction of the rate of muscle protein degradation and a reduction in the rate of cartilage degradation, as indicted by the observed levels of biomarkers for these degradative processes, i.e., levels of 3-methyl histidine are correlated with muscle protein degradation and levels of 4-hydroxy proline are correlated with cartilage degradation.

As demonstrated by the data of Tables 9 and 10, feeding canines the Anti-Aging Food of Table 4, resulted in a significant decline in the levels of post-translationally modified amino acids which are markers of these degradative process (3-methyl-histidine for muscle protein and 4-hydroxy proline for cartilage degradation). This reduction was apparent in the dogs fed the Anti-Aging Food, both as compared to baseline data (Day 0) as well as to the levels observed in control dogs fed the Control Food.

TABLE 9

Relative Concentration of 3-Methyl Histidine Levels

| | Day 0 | Day 45 |
|---|---|---|
| Control Food | 1 | 0.8 |
| Anti-Aging Food | 1 | 0.7 |

While both groups of treated dogs experienced a decline in 3-methyl histidine levels, indicating an improvement in the rate and/or extent of muscle protein, the treated dogs fed the Anti-Aging Food of Table 4 had a greater decline.

Accordingly, administration of a composition of the invention is useful as a method for prevention and/or treatment of age-related conditions in companion animals involving excessive degradation of muscle protein in an animal in need thereof.

TABLE 10

Relative Concentration of 4-Hydroxy Proline Levels

| | Day 0 | Day 45 | Day 90 |
|---|---|---|---|
| Control Food | 1 | 0.75 | 0.59 |
| Anti-Aging Food | 1 | 0.22 | 0.20 |

While both groups of treated dogs experienced a decline in 4-hydroxyproline levels, indicating an improvement in the rate and/or extent of cartilage degradation, the dogs fed the Anti-Aging Food of Table 4 had a greater decline.

Accordingly, administration of a composition of the invention is useful as a method for prevention and/or treatment of age-related conditions in companion animals involving excessive degradation of cartilage in an animal in need thereof.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. All percentages expressed herein are by weight of the composition on dry matter basis unless specifically stated otherwise.

What is claimed is:

1. A method of treating or preventing an age-related condition in a companion animal in need thereof, the method comprising
    administering to the animal an effective amount of a composition comprising a protein source, a carbohydrate source, a vegetable source, and a fruit source;
    wherein the protein source is a combination of chicken, egg protein in an amount of from about 4 wt % to about 15 wt %, based on a total weight of the composition on a dry matter basis, and corn gluten meal;
    wherein the carbohydrate source is a combination of millet, brewers rice, and oat groats;
    wherein the vegetable source is a combination of carrots, spinach, and tomato pomace;
    wherein the fruit source is citrus pulp;
    wherein the composition is a nutritionally complete diet for an adult companion animal;
    wherein the age-related condition comprises oxidative damage; and
    wherein treating or preventing the age-related condition in the companion animal in need thereof results in an improvement in oxidative defenses; and
    wherein the adult companion animal is a canine, and measuring an increase in one or more of peroxiredoxin-1 levels, proteasome levels, and ceruloplasmin levels after administering the nutritionally complete diet to the canine.

2. The method of claim 1, wherein the composition comprises the corn gluten meal in an amount from 6% to 20% based on the total weight of the composition on a dry matter basis.

3. The method of claim 1, wherein the composition comprises the vegetable source in an amount from 0.5% to 2% based on the total weight of the composition on a dry matter basis.

4. The method of claim 1, wherein the composition comprises the fruit source in an amount from 0.5% to 2% based on the total weight of the composition on a dry matter basis.

5. The method of claim 1, wherein the composition comprises the carbohydrate source in an amount from 5% to 50% based on the total weight of the composition on a dry matter basis.

6. The method of claim 1, wherein the oxidative damage of the age-related condition comprises a decrease in peroxiredoxin-1 levels in the companion animal.

7. The method of claim 6, wherein the improvement in oxidative defenses comprises an increase in peroxiredoxin-1 levels in the companion animal.

8. The method of claim 6, wherein the improvement in oxidative defenses comprises a 3.92-fold increase in peroxiredoxin-1 levels in the companion animal.

9. The method of claim 8, wherein the nutritionally complete diet is administered to the animal for 180 days, and wherein the method further comprises measuring an increase in peroxiredoxin-1 levels after administering the nutritionally complete diet to the canine.

10. The method of claim 1, wherein the oxidative damage of the age-related condition comprises a decrease in ceruloplasmin levels in the companion animal.

11. The method of claim 10, wherein the improvement in oxidative defenses comprises an increase in ceruloplasmin levels in the companion animal.

12. The method of claim 10, the improvement in oxidative defenses comprises a 2.15-fold increase in peroxiredoxin-1 levels in the companion animal.

13. The method of claim 12, wherein the nutritionally complete diet is administered to the animal for 180 days.

14. The method of claim 10, wherein the improvement in oxidative defenses comprises an increase in proteasome levels in the companion animal.

15. The method of claim 10, wherein the improvement in oxidative defenses comprises a 1.39-fold increase in proteasome levels in the companion animal.

16. The method of claim 15, wherein the nutritionally complete diet is administered to the animal for 180 days.

17. The method of claim 1, wherein the oxidative damage of the age-related condition comprises a decrease in proteasome levels in the companion animal.

18. A method for treating an age-related condition in a canine in need thereof, the method comprising:
    treating the age-related condition by administering to the canine in need thereof a nutritionally complete diet comprising a protein source, a carbohydrate source, a vegetable source, and a fruit source,
    wherein the age-related condition comprises oxidative damage,
    wherein the oxidative damage comprises a decrease in peroxiredoxin-1 levels,
    wherein the protein source comprises a combination of chicken, egg protein, and corn gluten meal,
    wherein the carbohydrate source comprises a combination of millet, brewers rice, and oat groats,
    wherein the vegetable source comprises a combination of carrots, spinach, and tomato pomace, and
    wherein the fruit source comprises citrus pulp; and
    measuring an increase in peroxiredoxin-1 levels after administering the nutritionally complete diet to the canine.

19. The method of claim 18, wherein the nutritionally complete diet is administered to the canine for 180 days, and wherein measuring the increase in peroxiredoxin-1 levels comprises measuring a 3.92-fold increase in peroxiredoxin-1 levels in the companion animal after 180 days.

20. A method for treating an age-related condition in a canine in need thereof, the method comprising:
    treating the age-related condition by administering to the canine in need thereof a nutritionally complete diet comprising a protein source, a carbohydrate source, a vegetable source, and a fruit source,
    wherein the age-related condition comprises oxidative damage,
    wherein the oxidative damage comprises a decrease in ceruloplasmin levels,
    wherein the protein source comprises a combination of chicken, egg protein, and corn gluten meal;
    wherein the carbohydrate source comprises a combination of millet, brewers rice, and oat groats;
    wherein the vegetable source comprises a combination of carrots, spinach, and tomato pomace; and
    wherein the fruit source comprises citrus pulp; and
    measuring an increase in ceruloplasmin levels in the canine after administering the nutritionally complete diet to the canine in need thereof.

21. The method of claim 20, wherein the nutritionally complete diet is administered to the canine for 180 days, wherein measuring the increase in the ceruloplasmin levels comprises measuring a 3.92-fold increase in the ceruloplasmin levels in the companion animal, and wherein the increase in the ceruloplasmin levels is measured after administrating the nutritionally complete diet to the canine for 180 days.

22. The method of claim 20, wherein the oxidative damage further comprises a decrease in peroxiredoxins-1 levels, wherein the nutritionally complete diet is administered to the canine for 180 days, wherein the method further comprises measuring an increase in peroxiredoxins-1 levels in the canine after administering the nutritionally complete diet to the canine in need thereof for 180 days.

* * * * *